United States Patent [19]

Barthomeuf

[11] Patent Number: 4,593,150

[45] Date of Patent: Jun. 3, 1986

[54] PROCESS FOR ENHANCING THE SEPARATION OF PARAXYLENE FROM A FEEDSTREAM CONTAINING OTHER XYLENES AND ETHYLBENZENE USING A ZEOLITE ADSORBENT

[75] Inventor: Denise M. Barthomeuf, Lyons, France

[73] Assignee: Exxon Research and Engineering Co., Florham Park, N.J.

[21] Appl. No.: 674,187

[22] Filed: Nov. 23, 1984

[51] Int. Cl.$^4$ ............................................. C10C 7/13
[52] U.S. Cl. ................................. 585/828; 208/310 Z
[58] Field of Search ...................... 208/310 Z; 585/828

[56] References Cited

U.S. PATENT DOCUMENTS

| | | | |
|---|---|---|---|
| 3,130,007 | 4/1964 | Breck. | |
| 3,558,732 | 1/1971 | Neuzil | 585/825 |
| 3,636,121 | 1/1972 | Stine et al. | 585/828 |
| 3,686,342 | 8/1972 | Neuzil | 208/310 Z |
| 3,686,343 | 8/1972 | Bearden, Jr. et al. | 208/310 Z |
| 3,698,157 | 10/1972 | Allen et al. | 208/310 Z |
| 3,734,974 | 5/1973 | Neuzil | 208/310 Z |
| 3,795,711 | 3/1974 | Worrell et al. | 585/828 |
| 3,835,043 | 9/1974 | Geissler et al. | 208/310 Z |
| 3,855,333 | 12/1974 | Neuzil | 208/310 Z |
| 3,878,127 | 4/1975 | Rosback | 585/828 |
| 3,894,108 | 7/1975 | Geissler | 208/310 Z |
| 3,903,187 | 9/1975 | Geissler | 208/310 Z |
| 3,943,182 | 3/1976 | Neuzil et al. | 585/828 |
| 3,998,901 | 12/1976 | Neuzil et al. | 208/310 Z |
| 4,265,788 | 5/1981 | Ebitani et al. | 208/310 Z |
| 4,283,587 | 8/1981 | Rosback et al. | 585/828 |
| 4,351,981 | 9/1982 | Smolia | 585/828 |
| 4,393,266 | 7/1983 | Smolin | 585/828 |

*Primary Examiner*—John Doll
*Assistant Examiner*—Glenn A. Caldarola
*Attorney, Agent, or Firm*—E. Thomas Wheelock

[57] ABSTRACT

Paraxylene is separated from a feedstream containing ethylbenzene and other xylenes by contacting the feedstream preferably with a K-substituted Type Y zeolite, passing through the zeolite a selected additive, and recovering a stream enhanced in concentration of paraxylene relative to ethylbenzene. Preferably, the additive is a cyclic nitrogen containing compound such as pyrrole or pyridine.

24 Claims, No Drawings

PROCESS FOR ENHANCING THE SEPARATION OF PARAXYLENE FROM A FEEDSTREAM CONTAINING OTHER XYLENES AND ETHYLBENZENE USING A ZEOLITE ADSORBENT

FIELD OF THE INVENTION

This invention relates to a process for enhancing the separation of paraxylene from a feedstream containing other xylenes and ethylbenzene wherein a KY (or possibly a NaY) zeolite is employed as the selective adsorbent for the paraxylene. These enhancements are due generally to the inclusion of a cyclic-nitrogen-containing additive, such as pyrrole or pyridine, to the adsorptive mixture. The addition may also cause the result of simultaneously improving the performance of the desorbents when such are used.

BACKGROUND OF THE INVENTION

Some crystalline aluminosilicates, or zeolites, are useful as adsorbents in separating certain hydrocarbon compounds from mixtures containing those compounds. In particular, zeolites are widely used for selective separation of paraxylene from mixtures with other $C_8$ aromatic compounds such as metaxylene, orthoxylene, ethylbenzene. For example, U.S. Pat. Nos. 3,636,121; 3,686,342; 3,686,343; 3,835,043; 3,855,333; 3,878,127; 3,894,108; 3,903,187 and 4,265,788 are all directed toward methods of separating paraxylene from mixtures with various hydrocarbons or of selectively obtaining paraxylene and ethylbenzene from a mixture containing other components, using various types of zeolites as adsorbents.

Paraxylene is a commercially important aromatic hydrocarbon since its use in the manufacture of terephthalic acid is a critical step in the subsequent production of various fibers such as Dacron.

This invention relates generally to a process for separating paraxylene from mixtures of other $C_8$ aromatics by selectively adsorbing the paraxylene on a faujasite zeolite, particularly sodium or potassium exchanged Y zeolites. The paraxylene is desorbed either through the use of cyclic hydrocarbonaceous molecules containing a nitrogen atom either alone or in combination with other desorbents such as benzene or paradiethylbenzene.

It is known that potassium-substituted Type Y zeolites having the faujasite structure selectively adsorb ethylbenzene from mixtures comprising ethylbenzene, metaxylene and orthoxylene using toluene as a desorbent. U.S. Pat. No. 3,998,901 teaches that ethylbenzene can be separated from xylene isomers using a Type Y zeolite substituted with Sr and K wherein ethane or lower gases or toluene is used as desorbent. According to U.S. Pat. No. 3,943,182, desorbents other than toluene, such as diethylbenzene or benzene, selectively separate ethylbenzene from a mixture containing ethylbenzene and at least one xylene isomer using a Type X zeolite. It is also disclosed that selectivity for ethylbenzene over its isomers decreases as the silica to alumina ratio in the zeolite is increased above 3.0 (i.e., using a Type Y zeolite).

U.S. Pat. No. 3,943,182 further teaches that the presence of water in the zeolite in amounts of 0.02 to 2.5% by weight measured by loss on ignition at 500° C. optimizes selectivity for ethylbenzene. Other patents disclose that certain compounds will modify the adsorbent characteristics of zeolites when contacted therewith. For example, in the context of aromatic isomer separation, U.S. Pat. No. 3,698,157 discloses that an organic radical-substituted silane modifies the characteristics of a selected zeolite in the separation of $C_8$ aromatic isomers. In U.S. Pat. No. 3,734,974 it is taught that faster exchange rates and reduced orthoxylene and metaxylene tailing are accomplished by adding small amounts of water to a particular adsorbent. Moreover, U.S. Pat. No. 3,855,333 is directed to use, as an adsorbent, of a zeolite containing 0.1 to 8.0% by weight of an alcohol to obtain increased selectivity of the zeolite for adsorption of paraxylene.

U.S. Pat. No. 4,283,587 to Rosback, issued Aug. 11, 1981, discloses a process for enhancing the selectivity of various substituted (usually potassium or barium substituted) Type X or Y zeolites for paraxylene over other $C_8$-aromatics. By preloading the zeolite with an alkyl amine hydrochloride or alkyl amine, the activity of the desorbents (particularly that of paradiethylbenzene) for removal of the adsorbed aromatic from the zeolite is improved as well.

U.S. Pat. No. 4,351,981 to Smolin, issued Sept. 28, 1982, discloses a process for the separation of paraxylene from mixtures of $C_8$-aromatics by contacting the mixture with either a pyridine-modified LiX or NaX zeolite. The process involves preferably preloading the zeolite with an amount of pyridine in an amount of about 10% to 60% of the total adsorptive capacity of the zeolite, e.g., preferably 3–6 wt.% based on the zeolite weight. The process is said to adsorb the $C_8$-aromatics to the exclusion of paraxylene. Consequently, it is said to be desirable to minimize the amount of the $C_8$-aromatics other than paraxylene by, e.g., distillation, prior to treating the stream with the modified zeolites. The pyridine may be used with another desorbent which preferably is toluene.

Similarly, U.S. Pat. No. 4,393,266 to Smolin, issued July 17, 1983 (the continuation-in-part of Smolin '981) suggests a similar process for separating paraxylenes from mixtures of $C_8$-aromatics using a pyridine treated zeolite. In this instance, however, the zeolite is NaY instead of LiX or NaX. As in the above-noted process, the zeolite adsorbs the other $C_8$-aromatics to the substantial exclusion of paraxylene.

U.S. patent application Ser. No. 426,242 by Hulme and Barthomeuf teaches the use of various adjuncts including water, alcohols, ammonia and pyrrole adsorbents used to recover ethylbenzene from KY zeolites. The feedstream treated by these zeolites is taught to be substantially depleted in paraxylene.

SUMMARY OF THE INVENTION

The invention disclosed herein is generally directed to a process for selectively adsorbing paraxylene from steams containing both ethylbenzene and mixtures of other isomeric xylenes. The process utilizes sodium or potassium substituted Type Y zeolites and certain cyclic additives whose ring contains a nitrogen atom. The cyclic additives may be used alone as the desorbent or in conjunction with other primary desorbents such as benzene or paradiethylbenzene. The additives may be selected from the group consisting of pyridine, 2-picoline, 3-picoline, 4-picoline, 2,4-lutidine, 2,6-lutidine, 3,4-lutidine, pyrrole, substituted pyrroles, and mixtures thereof. The preferred additives are pyridine and pyrrole with pyrrole being especially desirable. In addition, it is found that the use of the cyclic additive may optimize the strength of a primary desorbent without adversely affecting the selectivity factor of the zeolite for paraxylene over ethylbenzene for purposes of maximizing recovery of paraxylene.

Paraxylene may be separated and recovered from a feedstream mixture also contaning ethylbenzene and optionally orthoxylene and metaxylene by a process having the steps of (a) contacting the mixture with a sodium or potassium-substituted Type Y zeolite under conditions to effect the selective adsorption of the paraxylene by the zeolite, (b) passing through the zeolite, before, during or after the contacting step, a nitrogen containing cyclic hydrocarbon additive, such as pyrrole or pyridine, and with or without a primary desorbent such as benzene or paradiethylbenzene, and (c) recovering from the zeolite a stream enhanced in concentration of paraxylene.

The selectivity factor, which represents the selectivity of the adsorbent for paraxylene over ethylbenzene or isomeric xylenes, is defined by the expression:

$$\alpha\ Px/(ox,mx,eb) = \frac{\text{Amount of paraxylene in zeolite}}{\text{Amount of paraxylene in the unadsorbed phase}} \times \frac{\text{Amount of (orthoxylene, metaxylene, or ethylbenzene) in the unadsorbed phase}}{\text{Amount of (orthoxylene, methaxylene, or ethylbenzene) in zeolite}}$$

The desorbent strength factor, which represents the selectivity of the adsorbent for paraxylene over a desorbent, is defined by the expression:

$$\alpha\ px/\text{desorbent} = \frac{\text{Amount of paraxylene in zeolite}}{\text{Amount of paraxylene in the unadsorbed phase}} \times \frac{\text{Amount of desorbent in the unadsorbed phase}}{\text{Amount of desorbent in zeolite}}$$

DESCRIPTION OF THE PREFERRED EMBODIMENTS

The feedstream mixtures which are applicable to the present invention contain at least paraxylene and ethylbenzene but may also contain orthoxylene and metaxylene. Other components which may be present in the mixture include other aromatic hydrocarbons such as alkyl-substituted benzenes. In addition, the feedstream mixture may contain up to about 20 volume percent, but preferably less than about 10 volume percent, of non-aromatic components such as paraffins or cycloaliphatic or olefinic compounds. Such components will tend to be least adsorbed by the zeolites. It is noted, however, that whenever other components may be contained in the mixture, the process herein embodies a technique for separating paraxylene from ethylbenzene.

A feedstream mixture containing several $C_8$ aromatic isomers such as ethylbenzene and the xylene isomers is generally obtained, e.g., through reforming, pyrolysis or isomerization process. Paraxylene is often separated from this mixture by processes such as by crystallization or extraction of paraxylene.

In the process described herein, the paraxylene is separated from the ethylbenzene in the feedstream mixture by contacting the mixture with the zeolite adsorbent defined below such that the paraxylene is more selectively adsorbed than the ethylbenzene. Prior to, concurrently with this contacting step, or subsequent thereto (if the operation is a batch operation), a nitrogen containing cyclic additive stream is passed through the zeolite (in some instances in the presence of a primary desorbent phase) so as to desorb the adsorbed phase which has been enriched in paraxylene.

It will be recognized that contacting of the zeolite with the feedstream mixture the cyclic nitrogen containing additive and (optionally) the desorbent stream may be conducted in a batch or continuous mode of operation. For example, the adsorbent may be employed as a dense compact fixed bed which is alternately contacted with the feedstream mixture, additive, and desorbent or may be a fluidized bed contacted with the mixture, additive, and desorbent in a continuous operation with or without magnetic stabilization and with or without real or simulated co- or countercurrent flows. Where the adsorbent is employed as a single static bed it may be semi-continuous, i.e., operated as a pulsed chromatographic process; or a set of two or more static beds may be employed such that the feedstream mixture is contacted with one bed while the desorbent in passed through the other. The additive may be passed through the zeolite either with the desorbent or with the feedstream. It may be desirable to remove the least-adsorbed components from the voids in the bed by flushing with a very weakly adsorbed material, e.g., a paraffin, before recovery of the paraxylene. Moving or simulated moving beds represent, however, a preferred mode of operation because of the greater efficiency in separation obtained.

Temperatures for the contacting and desorption steps of the process herein may very broadly depending, for example, on the desorbent used, but generally will range from about room temperature to about 300° C. Similarly, operating pressures will vary considerably, usually from atmospheric to about 30 atm (3 megapascals) in pressure.

The additive employed in this process may be a nitrogen atom containing cyclic compound selected from the group consisting of pyridine, 2-picoline, 3-picoline, 4-picoline, 2,4-lutidine, 2,6-lutidine, 3,4-lutidine, pyrrole, substituted pyrroles, and mixtures thereof. The preferred additives are pyridine and pyrrole, particularly pyrrole. The additive or additives may be used alone or in combination with other known strong or primary desorbents such as benzene or paradiethylbenzene. The nitrogenous cyclic compound may be used in amounts up to about 12% by weight of the feedstream, preferably 3% to 10%. Pyrrole enhances the $\alpha PX/EB$ of the noted zeolites when used alone at concentrations up to 12%. These nitrogenous compounds also enhance or create selectivity for paraxylene over ethylbenzene when used with other desorbents such as paradiethylbenzene. As will be demonstrated below in the Examples, when benzene is used alone as a desorbent in $C_8$ aromatic separation or certain Type Y zeolites, the zeolite is selective for ethylbenzene over paraxylene. Addition of one of the nitrogenous compounds to the benzene inverts the selectivity of the zeolite to make it paraxylene selective in comparison to ethylbenzene. The separation between paraxylene and ethylbenzene is the most difficult to perform. For economically viable processes, the separation factor $\alpha pb/eb$ desirably should be greater than 2.0. Although, for the difficult paraxylene-ethylbenzene separation, a factor as low as 1.3 may be acceptable.

Another parameter of the combined additive desorbent stream which is improved by use of the nitrogenous compound is expressed by a desorbent strength factor, designated $\alpha_{px/desorbent}$ and defined above. This factor represents the ratio of the adsorption strength of the zeolite for the paraxylene to the adsorption strength of the zeolite for the desorbent. If the desorbent is too strong relative to paraxylene so that $\alpha_{px/desorbent}$ is less than, e.g., 0.1, both ethylbenzene and paraxylene will be eluted in overlapping peaks. On the other hand, a weak desorbent, with $\alpha_{px/desorbent}$ greater than 10, will not compete favorably with the paraxylene, necessitating large volumes of desorbent to recover all the paraxylene. The paraxylene thus collected would be contained in large amounts of the desorbent so that expensive distillation procedures would be required to recover the paraxylene. In other processes, the ratio should be in the region of 1–2, but for this difficult separation, a slightly lower value, e.g., 0.5, may be acceptable.

The zeolite adsorbent to be employed in the process of this invention preferably is a synthetic crystalline aluminosilicate of Type Y (having the faujasite structure) containing potassium or, optionally, sodium as the cation. The Type Y zeolites are described in U.S. Pat. No. 3,130,007, the disclosure of which is incorporated herein by reference. For purposes of the present invention a useful representative hydrated zeolite used as starting material is of the formula, which is not intended to be limiting in any respect:

$$(0.9 \pm 0.2)K_2O:Al_2O_3:wSiO_2:xH_2O$$

wherein w is a value greater than about 3 and x is any value up to about 9. Sodium may be utilized in the place of the noted potassium.

After the feedstream mixture and desorbent stream have have been contacted with the zeolite, the respective eluted product streams containing the various components are directed to separate collection vessels. The stream recovered, which is enhanced in the amount of paraxylene relative to ethylbenzene in the mixture (due to the separation achieved by the adsorption and desorption operations) may be processed so as to recover the paraxylene as by, e.g., distillation from the desorbent or by other suitable recovery techniques.

The following examples further illustrate the efficacy of the present invention. In these examples all parts and percentages are given by weight and all temperatures are in degrees Centigrade unless otherwise indicated.

EXAMPLE I

A series of feeds was prepared containing equimolar amounts of ethylbenzene, orthoxylene, metaxylene, and paraxylene and the percentage by weight of the hydrocarbon desorbent indicated in Table I.

Sodium or potassium Type Y faujasites were dried at 550° C. in a stream of dry nitrogen (containing less than 5 ppm $H_2O$), so that the zeolites lost 1.5% of this weight on ignition at 1000° C. Approximately 300 mg. samples of the zeolites were transferred to a series of 2-ml. vials sealed with a septum cap. To each bottle was added, by syringe, the respective feed in an amount representing the capacity of the zeolite. The vials were agitated at room temperature for 24 hours under ambient conditions. The vapor phase in equilibrium with the zeolite was analyzed by gas chromatography. From the peaks in the gas chromatograms the factors as defined above were determined and are indicated in Table I.

The methanol and ammonia additives were provided for the purpose of comparison.

TABLE I

| Zeolite | Additive (Wt %) | $\alpha \frac{px}{eb}$ | $\alpha \frac{px}{mx}$ | $\alpha \frac{px}{ox}$ |
|---|---|---|---|---|
| KY | None | 2 | 7.2 | 8.5 |
|  | Pyrrole (4%) | 2.3 | 8.5 | 8.2 |
|  | Pyrrole (8%) | 2.8 | 7.9 | 7.0 |
|  | Pyridine (4.6%) | 1.8 | 7.0 | 8.3 |
|  | Pyridine (9%) | 2.4 | 7.7 | 9.1 |
|  | Methanol (3.5%) | 1.8 | 6.5 | 6.7 |
|  | Methanol (9%) | 2.2 | 5.5 | 5.1 |
|  | Ammonia (4%) | 1.7 | 5.5 | 4.3 |
|  | Ammonia (8%) | 1.7 | 5.8 | 3.7 |
| NaY | None | 2.0 | 0.3 | 0.8 |
|  | Pyrrole (5.2%) | 2.8 | 0.4 | 0.9 |
|  | Pyrrole (8.7%) | 3.2 | 0.7 | 1.1 |
|  | Pyridine (5.2%) | 1.8 | 0.4 | 0.6 |
|  | Pyridine (12.5%) | 1.6 | 0.6 | 0.6 |

Pyrrole increases $\alpha px/eb$ for both zeolites.

EXAMPLE II

This example illustrates and compares the effect of adding pyridine or pyrrole to other desorbents and their effect on the zeolite KY selectivity for paraxylene over ethylbenzene.

The procedure of Example I was again followed using the a KY zeolite and adding to the zeolite before contacting it with the feed, the amount of methanol, pyrrole, or pyridine indicated in Table II. The $\alpha_{px/eb}$ and $\alpha_{px/desorbent}$ factors are indicated in the table.

TABLE II

KY Zeolite - Feed Equimolar $C_8$ Aromatics: Desorbent

|  | $\alpha \frac{px}{eb}$ | $\alpha \frac{px}{mx}$ | $\alpha \frac{px}{ox}$ | $\alpha \frac{px}{Des}$ |
|---|---|---|---|---|
| $4C_8$ | 1.7 | 6.7 | 7.5 | — |
| $4C_8$: Benzene | 0.5 | 1.5 | 1.9 | 2.8 |
| $4C_8$: p-DEB[a] | 1.7 | 5.6 | 6.3 | <0.05 |
| Methanol |  |  |  |  |
| $4C_8$ (+ methanol)[b] 9% | 2.2 | 5.5 | 5.1 | — |
| $4C_8$: Benzene: + methanol[c] | 0.6 | 2.1 | 2.0 | 3.1 |
| $4C_8$: p-DEB: methanol[c] | 1.6 | 3.5 | 3.2 | 0.4 |
| Pyrrole |  |  |  |  |
| $4C_8$ (+ pyrrole)[b] | 2.5 | 7.9 | 6.5 | — |
| $4C_8$: Benzene (+ pyrrole)[b] | 1.3 | 2.4 | 2.1 | 4.0 |
| $4C_8$: p-DEB (+ pyrrole)[b] | 2.7 | 5.1 | 4.5 | 0.8 |
| Pyridine |  |  |  |  |
| $4C_8$ (+ pyridine)[b] 9% | 2.4 | 7.7 | 9.1 | — |
| $4C_8$: Benzene (+ pyridine)[b] | 1.7 | 5.0 | 7.4 | 12 |
| $4C_8$: p-DEB (+ pyridine)[b] | 2.6 | 7.5 | 8.3 | 0.7 |

[a]paradiethylbenzene
[b]8 to 10% preadsorbed methanol or pyridine or pyrrole
[c]Feeds containing 10 wt % methanol Both pyridine and pyrrole show improved $\alpha px/eb$ over any of the desorbents or additives benzene, paradiethylbenzene or methanol alone. Both pyridine and pyrrole also substantially improve the value of px/des as compared to the respective desorbents, either alone or with methanol. This combination of improved selectivities suggests a highly practical adsorption process. Both additives also invert the selectivity of the zeolite for paraxylene over ethylbenzene when benzene is used as the desorbent and reestablish the zeolite's intrinsic selectivity for paraxylene over ethylbenzene. Both improve the zeolite's $\alpha px/eb$ when used in conjunction with paradiethylbenzene. Similar improvements are not seen when methanol is used as the additive. The cyclic nitrogen containing additives are the only ones shown.

In summary, the present invention is seen to provide an improved process for separating paraxylene from ethylbenzene wherein a faujasite, preferably a potassium or, optionally, sodium substituted Type Y zeolite is employed as the selective adsorbent and wherein selected compounds such as pyrrole or pyridine are employed as the additives.

What is claimed is:

1. A process for separating paraxylene from a stream containing paraxylene and at least one other $C_8$-aromatic comprising the steps of:
    (a) contacting the stream with a potassium substituted Type Y zeolite under conditions for effecting the selective adsorption of the paraxylene by the zeolite;
    (b) passing through the zeolite, before, during or after the contacting step, a cyclic nitrogen-containing additive; and
    (c) recovering from the zeolite a stream enhanced in concentration of paraxylene relative to the other $C_8$-aromatic.

2. The process of claim 1 additionally comprising the step of passing a desorbent through the zeolite to recover the paraxylene.

3. The process of claim 2 wherein the other $C_8$-aromatic comprises ethylbenzene.

4. The process of claim 3 wherein the stream additionally contains at least one of orthoxylene and metaxylene.

5. The process of claim 1 wherein the cyclic nitrogen containing additive is selected from the group consisting of pyridine, 2-picoline, 3-picoline, 4-picoline, 2,4-lutidine, 2,6-lutidine, 3,4-lutidine, pyrrole, substituted pyrroles, and mixtures thereof.

6. The process of claim 5 wherein the cyclic nitrogen-containing additive is pyrrole.

7. The process of claim 5 wherein the cyclic nitrogen-containing additive is pyridine.

8. A process for separating paraxylene from a stream containing paraxylene and ethylbenzene comprising the steps of:
    (a) contacting the stream with a potassium substituted Type Y zeolite under conditions for effecting the selective adsorption of paraxylene by the zeolite;
    (b) passing through the zeolite, before, during or after the contacting step, a desorbent stream comprising benzene and a cyclic nitrogen-containing additive in a sufficient amount that $\alpha px/eb$ is greater than about 1.0; and
    (c) recovering from the zeolite a stream enhanced in concentration of paraxylene relative to ethylbenzene.

9. The process of claim 8 wherein the cyclic nitrogen containing additive is selected from the group consisting of pyridine, 2-picoline, 3-picoline, 4-picoline, 2,4-lutidine, 2,6-lutidine, 3,4-lutidine, pyrrole, substituted pyrroles, and mixtures thereof.

10. The process of claim 9 wherein the cyclic nitrogen containing additive is pyrrole.

11. The process of claim 9 wherein the cyclic nitrogen containing additive is pyridine.

12. The process of claim 8 wherein the stream also contains orthoxylene.

13. The process of claim 8 wherein the stream also contains metaxylene.

14. A process for separating paraxylene from a stream containing ethylbenzene and paraxylene but substantially no metaxylene or orthoxylene comprising the steps of:
    (a) contacting the stream with potassium substituted Type Y zeolite under conditions for effectively adsorbing paraxylene on the zeolite;
    (b) passing through the zeolite, before, during, or after the contacting step a cyclic nitrogen containing additive; and
    (c) recovering from the zeolite a stream enhanced in concentration of paraxylene relative to ethylbenzene.

15. The process of claim 14 wherein the cyclic nitrogen containing additive is selected from the group consisting of pyridine, 2-picoline, 3-picoline, 4-picoline, 2,4-lutidine, 2,6-lutidine, 3,4-lutidine, pyrrole, substituted pyrroles, and mixtures thereof.

16. The process of claim 15 wherein the cyclic nitrogen containing additive is pyrrole.

17. The process of claim 15 wherein the cyclic nitrogen containing additive is pyridine.

18. A process for enhancing the selectivity of a potassium substituted Type Y zeolite for adsorbing paraxylene over ethylbenzene when using paradiethylbenzene as a desorbent comprising the step of passing a cyclic nitrogen containing compound through said zeolite before, during, or after contacting the zeolite with a stream containing at least ethylbenzene and paraxylene.

19. The process of claim 18 wherein the cyclic nitrogen containing additive is selected from the group consisting of pyridine, 2-picoline, 3-picoline, 4-picoline, 2,4-lutidine, 2,6-lutidine, 3,4-lutidine, pyrrole, substituted pyrroles, and mixtures thereof.

20. The process of claim 19 wherein the enhanced selectivity, expressed as px/eb, is greater than about 2.0.

21. The process of claim 20 wherein the cyclic nitrogen containing compound is pyridine.

22. The process of claim 20 wherein the cyclic nitrogen containing compound is pyrrole.

23. The process of claim 19 wherein the stream additionally contains at least one of metaxylene and orthoxylene.

24. A process for separating paraxylene from a stream containing ethylbenzene, orthoxylene, metaxylene, paraxylene comprising the steps of:
    (a) contacting the steam with a potassium substituted Type Y zeolite under conditions for effectively selectively adsorbing paraxylene on the zeolite;
    (b) passing through the zeolite, during or after the contacting step, a desorbent stream containing up to 12 weight % benzene or p-diethylbenzene and 4 to 10 weight % pyrrole;
    (c) recovering from the zeolite a stream enhanced in concentration of paraxylene relative to ethylbenzene; and
    (d) separating paraxylene from the desorbent stream.

* * * * *